US00PP08813P

United States Patent [19]

Austin

[11] Patent Number: Plant 8,813

[45] Date of Patent: Jul. 5, 1994

[54] ROSE PLANT 'AUSVELVET'

[75] Inventor: David C. H. Austin, Albrighton, England

[73] Assignee: David Austin Roses Limited, Albrighton, England

[21] Appl. No.: 954,959

[22] Filed: Sep. 30, 1992

[51] Int. Cl.[5] ..... A01H 5/00

[52] U.S. Cl. ..... Plt./1

[58] Field of Search ..... Plt. 1, 28, 29

*Primary Examiner*—Howard J. Locker
*Assistant Examiner*—E. F. McElwain
*Attorney, Agent, or Firm*—Klarquist Sparkman Campbell Leigh & Whinston

[57] ABSTRACT

A bush rose variety having bushy growth, quartered flowers, floriferousness, and highly scented flowers.

1 Drawing Sheet

The present invention relates to a new and distinct variety of shrub rose plant name Ausvelvet of the shrub class which was originated by me by crossing the variety Lilian Austin, with the variety The Squire.

The primary objective of this breeding was to produce a new rose variety having quartered, red, scented flowers on a bushy plant and which repeats flowers. The objective was substantially achieved along with other desirable improvements as evidenced by the following unique combination of characteristics which are outstanding in the new variety and which distinguish it from its parents, as well as from all other varieties of which I am aware:

1. Bushy growth;
2. Quartered flowers;
3. Floriferousness; and
4. Highly scented flower.

Asexual reproduction of this new variety by budding, as performed at Albrighton, Wolverhampton, England, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with the Methuen Handbook of Color, except where ordinary dictionary significance of color is indicated.

Parentage:

*Seed parent.*—Lilian Austin.

*Pollen parent.*—The Squire.

Classification:

*Botanical.*—*Rosa hybrida.*

*Commercial.*—Shrub.

FLOWER

Observations made from specimens grown in a garden in Albrighton, Wolverhampton, England, in August of 1991.

Blooming habit: Recurrent.

Bud:

*Size.*—1½-2" when the petals start to unfurl.

*Form.*—Long, Globular, cuspidate apex.

*Color.*—When sepals first divide, bud color is 12E8 but more red. When half blown, the upper and lower sides of the outer petals are 12F/D8 Ruby (top) 12C8 Cerise to 12C7 Greyish Ruby at center of petal.

*Sepals.*—Color: Most of the sepal is 29D/E7 Greyish Green with Raspberry Red 10D7 and blush on midline and margin. Surface texture: Leathery, Spotty. There are three heavily appendaged sepals. There are two unappendaged sepals with hairy edges.

*Receptable.*—Color: 30E8 Parrot Green, 10D7 Red spots. Shape: Cup shaped. Size: Small, about ¼"×⅜". Surface: Spotty.

*Peduncle.*—Length: Medium. Surface: Glandular. Color: Medium Green 30D8 with Maroon 11F8 blushing. Strength: Bending.

Bloom:

*Size.*—Medium. Average open size is 2¾" in diameter.

*Borne.*—Singly, several together, in clusters of up to 12 flowers. If in clusters: Irregular shape.

*Stems.*—Medium. Average length is about 24–30".

*Form.*—When first open: Cupped, Flat. Permanence: Flattens, outer petals curl back.

*Petalage.*—Number of petals under normal conditions: 125.

*Color.*—The upper side of the petals is 13F7 Dark Magenta fading to 12E7 Greyish Magenta at top of petal and to 13C7-13C6 Greyish Magenta at center of petal. The reverse side of the petals is the same. The base of petals has a 2D4 Pastel Yellow tip. The major color on the upper side is Greyish Magenta 13C6.

*Variegations.*—None.

*Discoloration.*—The general tonality at the end of the first day: Slight greying. At the end of the third day: The color of the majority of the petals is 13F8 Dark Magenta fading to 13E8 Magenta at top and to 13C7 at the petal center.

*Fragrance.*—Strong, rich old rose.

Petals:

*Texture.*—Thin, silky.

*Shape.*—Apex round, deltoid.

*Form.*—Cupped, inner petals caught into space between perigynous zone and styles to form a button.

*Arrangement.*—Imbricated, with many petaloids in the center.

*Persistence.*—Petals hang on and dry.

*Lastingness.*—On the plant: 7-10 days. As a cut flower: 5-7 days.

Reproductive parts:

*Anthers.*—Size: Medium. Quantity: Many. Color: 3-4A8 tinged with Cerise 12C8. Arrangement: Tucked in calyx or partly so, mixed with petaloids.

*Filaments.*—Color: White, Pale Green 30A3 some Cerise 12C8 tinge.

*Pollen.*—Color: Gold Yellow.

*Styles.*—Color: Pale Green 30A3.

*Stigmas.*—Color: Yellow 3A5, some Cerise 12C8 streaks.

Form: Bush.

Growth: Medium, Branching.

Height: 30-36".

Foliage:

*Number of leaflets on normal mid-stem leaves.*—7.

*Size.*—Large, Medium, about 2" long×1¼" wide.

*Quantity.*—Normal.

*Color.*—New foliage: 30F7 Dark Green, Violet Brown 10F6 blush. Old foliage: 28F8 Dark Green.

Leaflets:

*Shape.*—Elliptic, cuspidate apex.

*Texture.*—Upper side: Leathery.

*Edge.*—Serrated.

*Serration.*—Single, Small.

*Petiole rachis.*—Color: Green.

*Petiole underside.*—Occasional prickles.

*Stipules.*—Medium, Serrated.

*Disease resistance.*—Resistant to mildew and blackspots under normal growing conditions at Albrighton, Wolverhampton, England.

Wood:

*New wood.*—Color: Dark Green 29E/F7 and Burgundy 12 F5 pigmentation raised in pustules. Bark: Roughish.

*Old wood.*—Color: Green, Brown and 12F7 Dark Ruby. Bark: Rough.

Prickles:

*Quantity.*—On main canes from base: Many. On laterals from main canes: Many.

*Form.*—Straight, hooked downward.

*Color when young.*—Red.

Small prickles:

*Quantity.*—On main stalks: Many. On laterals: Many.

*Color.*—Brown.

I claim:

1. A new and distinct variety of rose plant of the bush class, substantially as herein shown and described, characterized particularly as to novelty by the unique combination of its bushy growth, floriferousness, and highly scented flowers.

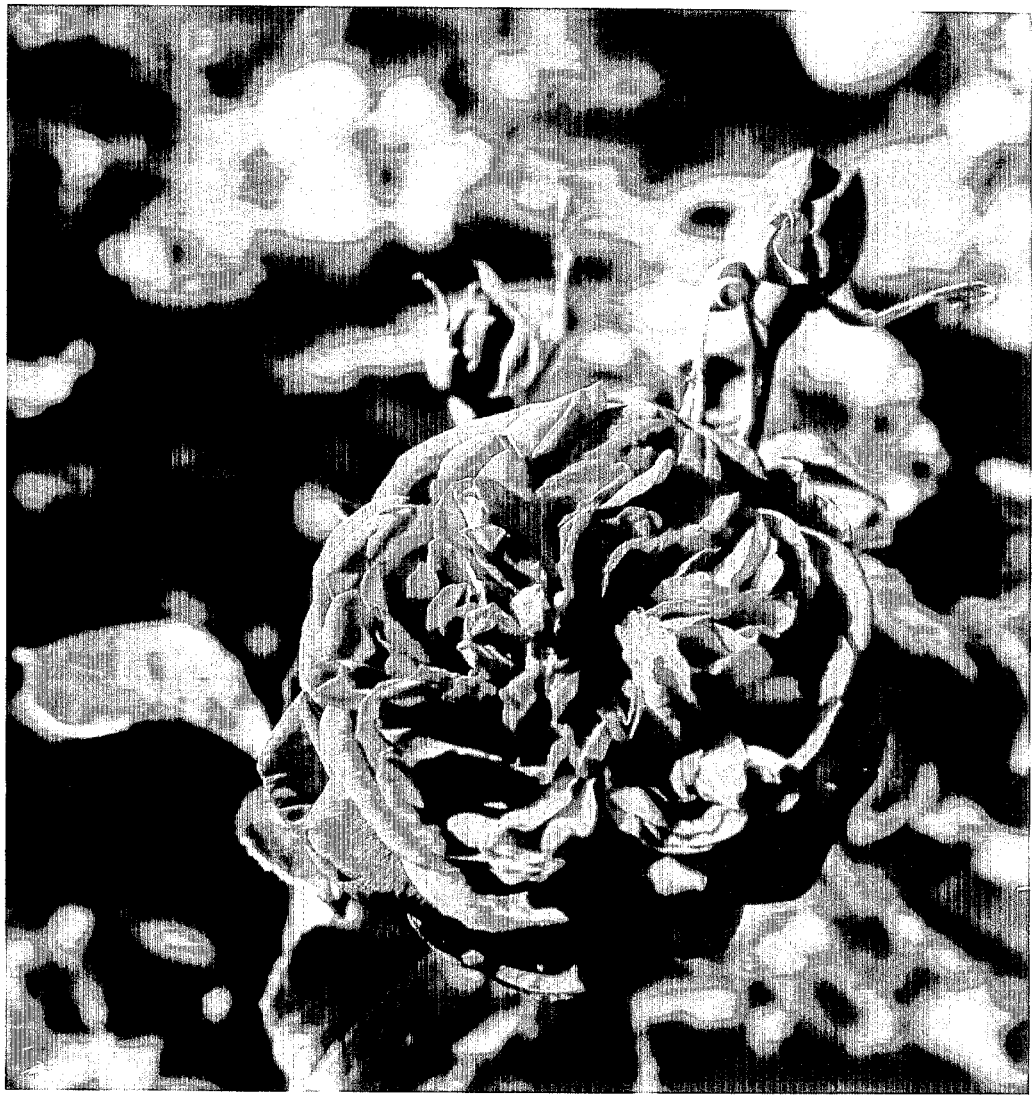

* * * * *